US005343290A

United States Patent [19]
Batchelder et al.

[11] Patent Number: 5,343,290
[45] Date of Patent: Aug. 30, 1994

[54] SURFACE PARTICLE DETECTION USING HETERODYNE INTERFEROMETER

[75] Inventors: John S. Batchelder, Somers; Donald M. DeCain, New York; Philip C. D. Hobbs, Briarcliff Manor; Marc A. Taubenblatt, Pleasantville, all of N.Y.

[73] Assignee: International Business Machines Corporation, Armonk, N.Y.

[21] Appl. No.: 897,198

[22] Filed: Jun. 11, 1992

[51] Int. Cl.$^5$ .............................................. G01B 9/02
[52] U.S. Cl. ........................................ 356/349; 356/237
[58] Field of Search ............... 356/345, 346, 349, 359, 356/360, 237, 371, 349; 250/571

[56] References Cited

U.S. PATENT DOCUMENTS

| | | | |
|---|---|---|---|
| 4,610,541 | 9/1986 | Tanimoto et al. | 356/237 |
| 4,669,875 | 6/1987 | Shiba et al. | 356/237 |
| 4,740,708 | 4/1988 | Batchelder | 250/563 |
| 4,848,908 | 7/1989 | Huang | 356/349 |
| 5,030,842 | 7/1991 | Koshinaka et al. | 250/571 |

FOREIGN PATENT DOCUMENTS

| | | | |
|---|---|---|---|
| 60-067845 | 4/1985 | Japan | G01N 21/88 |
| 60-224044 | 11/1985 | Japan | G01N 21/88 |
| 63-061152 | 3/1988 | Japan | G01N 21/89 |

OTHER PUBLICATIONS

G. Makosch et al., "Surface Profiling by Electro-Optical Phase Measurements", SPIE vol. 316, 1981, pp. 42–53.
"Doubly Darkfield Microscopy", IBM Technical Disclosure Bulletin, V. 30, N 6, Nov. 1987 p. 334.

*Primary Examiner*—Samuel A. Turner
*Assistant Examiner*—Robert Kim
*Attorney, Agent, or Firm*—Heslin & Rothenberg

[57] ABSTRACT

A heterodyne interferometer is combined with darkfield surface particle detection for improved surface particle detection sensitivity. The probe beam and the reference beam have different wavelengths. The reference beam may either be a real reference beam or a virtual reference beam. The probe beam may be incident at the surface at either a grazing angle or at an angle substantially normal to the surface. The real reference beam is incident at the surface at a grazing angle. The detection may either be conventional heterodyne detection or a combination of heterodyne and Lloyd's mirror detection.

26 Claims, 5 Drawing Sheets

SURFACE PARTICLE DETECTION USING HETERODYNE INTERFEROMETER

BACKGROUND OF THE INVENTION

The present invention relates to the detection of particles and asperities on a workpiece surface. Specifically, the invention combines a heterodyne interferometer with darkfield illumination or Lloyd's mirror detection for detecting particles or asperities on a surface.

Darkfield inspection tools are the current state-of-the-art particle detectors for surface contamination. These tools rely upon the technique of establishing a distinctive interference node at the workpiece surface using grazing angle illumination. As a result, only particles or features having a profile higher than the dominant mirror plane of the surface are illuminated and scatter light. Certain of the state-of-the-art particle detectors detect the scattered light at grazing angles by use of a process called a Lloyd's mirror. Even the latter technique causes particles or features to be preferentially detected the greater the profile from the workpiece surface.

All of these tools perform under the assumption that the detectors will not measure any light when there are no particles on the surface. Efforts are made to baffle out room lights and to absorb stray scatter to assure that no light is measured in the absence of particles on the surface. For many types of products being inspected, such as rough metal film surfaces, the scattered light from the film being inspected that reaches blackened surfaces within the inspection tool and is reflected to be scattered into the detectors is the dominant source of background light and is the primary limitation affecting detector sensitivity.

A problem arises when these darkfield techniques are attempted to be used in in-situ measurements. Namely, light must travel through windows in a processing chamber. Moreover, typical processing chambers are light reflecting and not light absorbing. Additionally, the process being performed in the chamber often causes light emission. The combined effect is that there are too many scattered light sources for in-situ particle inspection using darkfield measurement techniques.

In addition to in-situ measurement inside manufacturing process tools, it is sometimes desirable to detect particles or asperities on a surface in combination with other inspection processes. For example, an optical microscope review station fitted with a surface particle detector would enable an operator to rapidly assess both the existence and type of contamination present on the surface. The addition of a particle detector to a scanning electron microscope or focussed ion beam tool would allow both the morphology and composition measurement of particles to be made without requiring an initial detection of the particles and the subsequent realignment of the workpiece with sufficient accuracy to enable re-detection of the particles in the scanning electron microscope or focussed ion beam tool.

Doubly darkfield microscopy is described in an article entitled "Doubly Darkfield Microscopy" in IBM Technical Disclosure Bulletin, volume 30, no. 6, November 1987 at page 334. Darkfield scanning is disclosed in U.S. Pat. No. 4,610,541 entitled "Foreign Substance Inspecting Apparatus."

An apparatus useful for particle detection having the scattered beam and the reference beam at the same wavelength is described in U.S. Pat. No. 5,030,842 entitled "Fine-Particle Measuring Apparatus." The patent describes two detection systems. In one system both the reference beam and the probe beam are reflected from the surface and are combined at a detector. This brightfield-brightfield system is ineffective for particle detection because the signal produced at the photodetector will reproduce the original laser modulation, irrespective of whether a particle is present or not. In the other system the photodetector receives only darkfield scatter from the workpiece surface. While this configuration is operable, it does not produce stray light rejection, because there is no optical beam coherent with the darkfield scatter incident on the detector to produce either homodyne or heterodyne amplification of the scattered signal.

In another arrangement both the probe beam and the reference beam have the same wavelength, producing homodyne instead of heterodyne amplification. In this arrangement the probe beam is modulated in intensity. An embodiment comprises, for example, a Bragg cell which transmits light to the surface only when the RF drive signal to the cell is turned off, so that amplitude modulation of the RF signal to the Bragg cell, in turn, modulates the intensity of the probe beam. While operable this embodiment is not optimal. Interferometric amplification works only when the reference signal frequency and the signal to be amplified have the correct phase relationship. In heterodyne amplification, all possible phase relationships are detected because the reference signal and the signal to be amplified have different frequencies. In homodyne amplification, since the particle scatter signal can have random phase, the reference and the signal to be amplified will not interfere properly a substantial fraction of the time.

The present invention overcomes the described limitations by combining the stray light rejection capability of heterodyne techniques with the asperity detection capability of darkfield illumination with or without Lloyd's mirror detection.

SUMMARY OF THE INVENTION

In heterodyne detector methods, light scattered from a particle located on a workpiece surface will produce a detected signal that is proportional to the square of the electric fields radiated from the particle. If additional light is present at the detector and the additional light is spatially coherent with the light scattered from the particle, the resulting detected signal is proportional to the square of the sum of the two electric fields. Since the light scattered from a small particle will produce a spherical wavefront signal in the far field centered about the particle, the additional light or reference beam must likewise produce the same effective wavefront in order to achieve the desired squared amplification effect.

There are two methods of generating such a reference beam. One method is to focus a reference optical beam at the workpiece surface being inspected in the vicinity of the particle and to detect the beam reflecting from the surface in the detector. The detected signal scattered by this method will be referred to as a real reference signal. The other method is to optically arrange the reference wave fronts at the detector to be co-planar with the light scattered from the particle without the reference beam being incident on the workpiece surface. The detected signal by this method will be referred to as a virtual reference signal.

In accordance with the teachings of the present invention, the probe beam which generates the scattered field from the particle is at a different wavelength than the reference beam. When the scattered beam from the particle and the reference beam, which have two different wavelengths, are mixed at the detector, the interference between the two beams will result in a modulated signal at a frequency equal to the difference of the frequencies of the two optical beams, as is conventional in heterodyne detection.

The use of homodyne detection (where both the probe beam and reference beam are at the same wavelength or frequency) is less desirable because of a greater susceptibility to laser noise, background scatter, and microphonics. Moreover, scanning over patterned or rough features generates a high frequency modulation of the reference beam when the real reference beam method is used. In order to overcome the problem, the interferences or beat frequency between the probe beam and reference beam should be made at least an order of magnitude greater than the highest modulation frequency that can originate from scanning.

The real reference beam can be made incident to the workpiece at an angle of incidence nearly normal to the surface, at a grazing angle of incidence to the surface or at an angle between grazing and normal. A grazing angle shall be defined as an angle greater than 80° from an axis normal to the workpiece surface. Otherwise, the angle will be considered near normal. A virtual reference beam is similarly categorized. The virtual reference shall be referred to as grazing if the back propagation of the wave fronts reaching the detector would be incident on the workpiece surface at an angle greater than 80° from a axis normal to the workpiece surface. Otherwise the angle will be considered near normal.

Darkfield illumination and Lloyd's mirror detection occurs when light is incident at a surface at a nearly grazing angle, an interference pattern is formed between the incident light wave and the reflected light wave. The resulting electric field intensity I varies with the distance h from the surface according to the following equation:

$$I = 2I_o \left( 1 - \cos \frac{(4\pi h \cos \theta)}{\lambda} \right)$$

where $I_o$ is the intensity of the incident illumination, $\lambda$ is the optical wavelength and $\theta$ is the angle of incidence. At locations near the surface the equation simplified to:

$$I = \frac{16 I_o \pi^2 h^2 \cos^2 \theta}{\lambda^2}$$

The intensity I increases quadratically with the distance h from the surface. Therefore, rough or pattern features in the surface are not illuminated while asperities or particles that rise above the surface are illuminated.

Alternatively, assume there is a light source at a location h above a surface and a detector oriented so that it receives scattered light at an angle $\theta$ from an axis normal to the surface, and $I_o$ is the intensity that the detector would measure in the absence of the surface. The presence of the surface provides a second path to the detector. If $\theta$ is sufficiently close to 90° i.e. a grazing angle, there is a 180° phase shift of the reflected beam. The combined intensity from the incident light beam and the reflected light beam produced at the detector is defined by the above two equations. This effect is referred to as a Lloyd's mirror. That is, there is formed an interference in the far field between the directly incident light wave and the reflected light wave which creates interference fringes commencing with a null at grazing angles.

A preferred embodiment has the light source polarized perpendicular to the plane of incidence (S-polarized) because this configuration generally has the highest reflectivity and the phase shift is closest to 180 degrees.

The present invention relies upon the combination of heterodyne detection and darkfield illumination and Lloyd's mirror detection to achieve improved particle detection.

In theory the probe or incident illumination can be at a near normal angle or grazing angle of incidence, the reference beam can be at a near normal angle or grazing angle of incidence and the reference beam can be normally real or virtual, resulting in eight possible combinations. The following table shows the eight possibilities.

| Illumination | DETECTION | | | |
| --- | --- | --- | --- | --- |
| | Real Reference-Conventional Detection | Real Reference-Lloyd's Mirror | Virtual Reference-Conventional Detection | Virtual Reference-Lloyd's Mirror |
| Normal Angle Incident Beam | | + | | + |
| Grazing Angle Incident Beam | + | + | | + |

Only the five combinations with the plus sign (+) in the box pertain to the present invention.

The combination of a real reference beam and conventional detection is disregarded because the reference beam is required to be incident at the surface at a normal angle where it is reflected from the surface and is incident on the detector. Such an arrangement is conventional in many kinds of interferometric microscopes, e.g. Normarski, and introduces too much surface signal in the reference beam. The combination of a virtual reference beam incident at the surface at a normal angle and incident beam at a normal angle to the surface is disregarded because neither the incident beam nor the reference beam utilize the properties of grazing angle illumination or detection and hence, the combination provides no preference to signals arising from particles or asperities on the surface. The remaining five combinations provide a novel instrument with improved detection capabilities for particle detection.

A principle object of the present invention is therefore, the provision of a heterodyne darkfield surface particle detector having a probe beam and a reference beam of different wavelengths.

Another object of the invention is the provision of a heterodyne darkfield surface particle detector having a probe beam and a reference beam of different wavelengths where scattered light at a grazing angle is detected by a process called a Lloyd's mirror. The combination of darkfield illumination and Lloyd's mirror detection being referred to as doubly darkfield.

DETAILED DESCRIPTION

FIGS. 1 to 5 illustrate each of the five preferred combinations shown in the table above.

Figure 1:
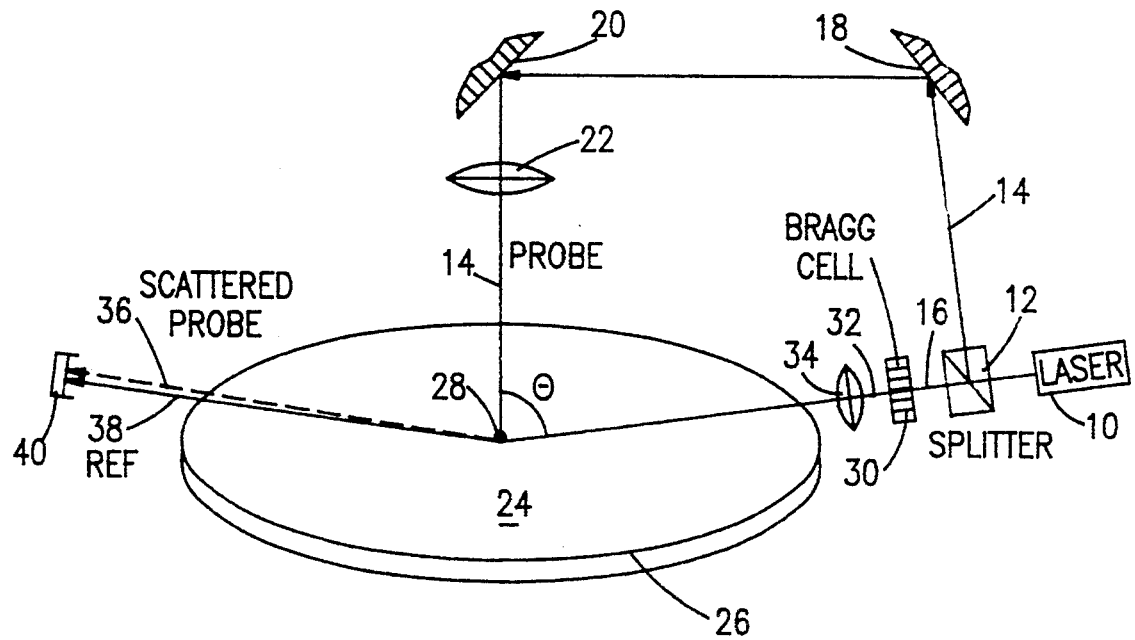
FIG. 1 is a schematic representation of a preferred embodiment of the present invention including a real reference beam, Lloyd's mirror detection and a normal angle probe beam.

Referring now to the figures and to FIG. 1 in particular, there is shown a schematic representation of an arrangement for detecting particles or asperities on a workpiece surface using a real reference light beam, Lloyd's mirror detection and a probe beam incident at the workpiece surface in direction substantially normal to the surface.

A laser 10 transmits a beam of energy at a wavelength $\lambda_1$, to a beam splitter 12 where the beam is split into two portions, probe beam 14 and beam 16. Probe beam 14 is reflected from reflector 18 and reflector 20 through lens 22 onto the surface 24 of workpiece 26. Probe beam 14 having wavelength $\lambda_1$, strikes the workpiece at angle substantially normal to the workpiece surface for illuminating particles or asperities 28 located on the surface.

The laser beam 16 enters a Bragg cell 30 where it is diffracted and the wavelength of the beam is changed to a value $\lambda_2$ so that the exiting reference beam 32 and the probe beam 14 have different wavelengths. The reference beam 32 travels through a lens 34 and is incident at the surface 24 at a grazing angle $\theta$, i.e. an angle greater than approximately 80° from an axis normal to the surface. The probe beam 14 and real reference beam 32 are focussed at substantially the same location on the surface 24.

When the beams encounter a particle 28, two beams, i.e. a scattered probe beam 36 at a first wavelength $\lambda_1$, and a reference beam 38 at a second wavelength $\lambda_2$ are received at a detector 40. In a preferred embodiment, the detector is a Lloyd's mirror, and is a square law electric field detector (such as a photodiode) which detects light scattered at a grazing angle so that the scattered and reference fields mix at the detector, generating the beat frequency signal at a frequency equal to the difference of the frequency between the scattered probe beam signal and the scattered reference beam signal.

The detection of the beat frequency signal provides improved signal-to-noise detection of signals arising from a surface particle since spurious noise arising from the laser or from background scatter or the like will be cancelled by the heterodyne detection scheme. The darkfield illumination afforded by the reference beam in the arrangement shown in FIG. 1 in combination with a Lloyd's mirror detector provides improved detection sensitivity.

Heterodyne detection is described in the article "Surface Profiling By Electro-Optical Phase Measurements" by G. Makosch et al, SPIE vol. 316, 1981, pages 42–53. Lloyd's mirror detection is described in the book "Principles of Optics" by M. Born and E. Wolf, N.Y. Fifth Edition, 1975, pages 262–263.

In a typical embodiment, the value of $\lambda_1$, is in a range between 195 nm to 1100 nm and the frequency of the beam having wavelength $\lambda_2$, is offset by a frequency in the range between 10 $KH_z$ and 1 $GH_z$ from the frequency of the beam having a wavelength $\lambda_1$, where $$f_1 = c \frac{\lambda_1}{n},$$

where c is the speed of light in a vacuum and n is the index of refraction of the medium through which the beam is travelling. The laser may be a solid state, gas, glass, or dye laser.

The output of the detector is a signal indicative of the presence of a particle or asperity on the workpiece surface at the location where the probe beam and reference beam intersect at a non-orthogonal angle $\theta$.

Figure 2:
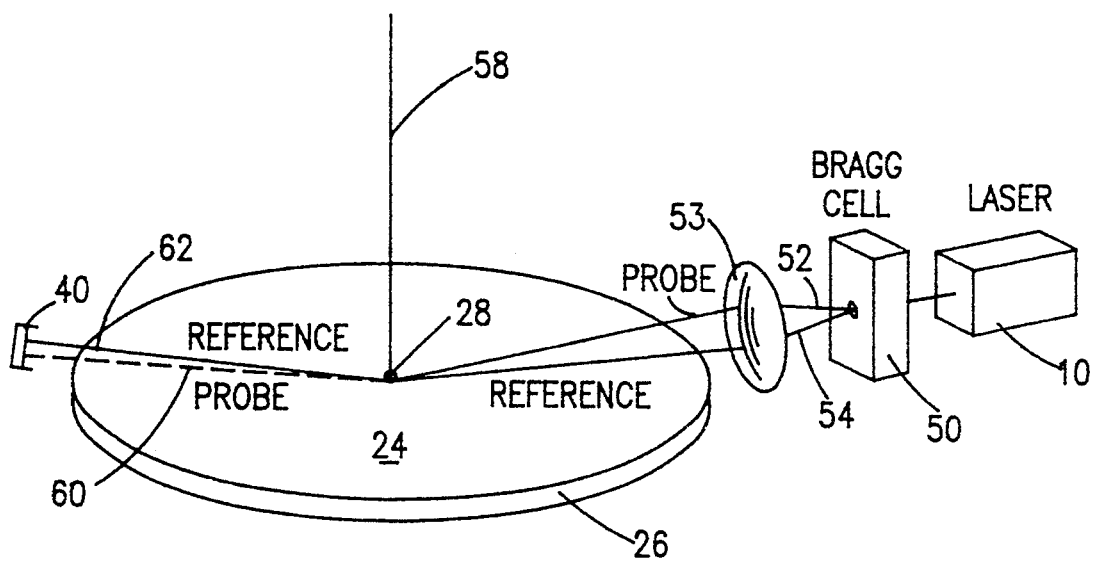
FIG. 2 is a schematic representation of another preferred embodiment of the invention including a real reference beam, Lloyd's mirror detection and a grazing angle probe beam.

FIG. 2 is a schematic representation of surface particle detection employing a real reference beam, Lloyd's mirror detection and a probe beam incident on the workpiece surface at a grazing angle.

Laser 10 transmits a beam of energy into a Bragg cell 50. Two laser beams 52, 54 exit the Bragg cell at different wavelengths and at different angles. A first beam 52, a probe beam, travels through lens 56 and is focussed at a location on the surface 24 of the workpiece 26 where there is a particle 28. A second beam 54, a reference beam, travels through lens 52 and is also focussed at a location on the surface of the workpiece 26 where there is a particle 28. Both the probe beam 52 and reference beam 54 are incident at the workpiece surface 24 at grazing angles. The two beams may be incident at the same or at different angles with respect to an axis 58 normal to the surface 24.

In a similar manner to that described in conjunction with the arrangement per FIG. 1, a scattered probe beam 60 and a scattered reference beam 62 from the particle 28 are received at Lloyd's mirror detector 40. The beat frequency signal is generated and particle 28 is detected.

Figure 3:
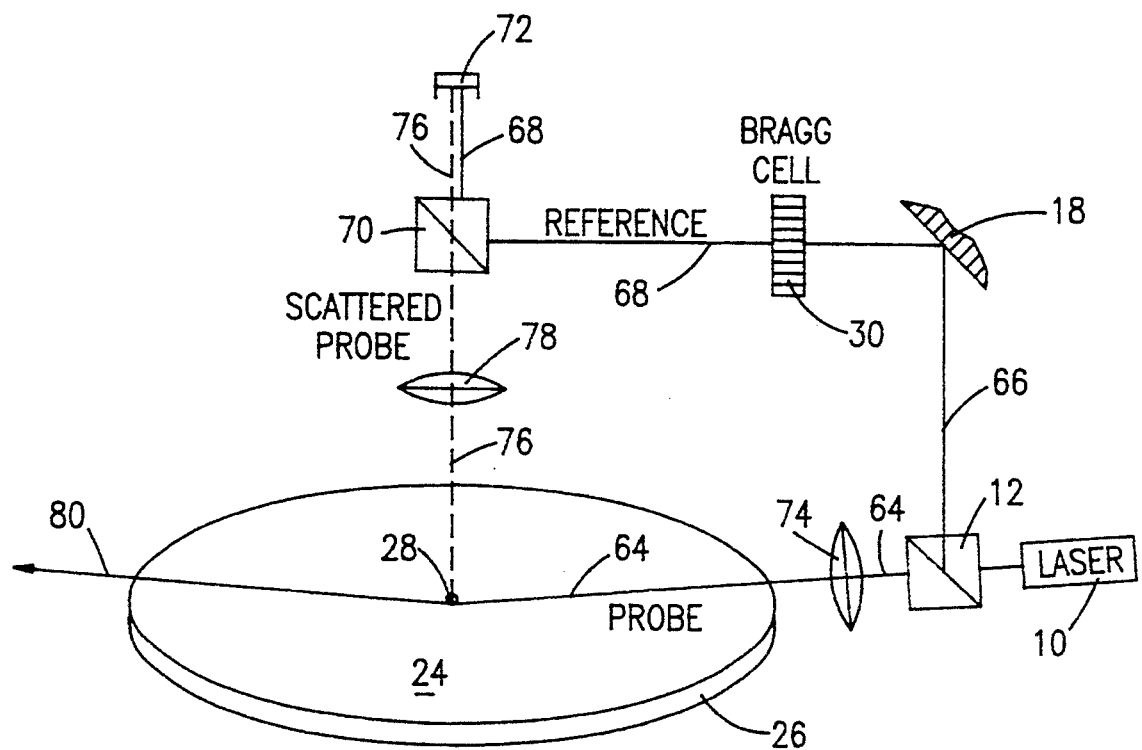
FIG. 3 is a schematic representation of another preferred embodiment of the invention including a virtual reference beam, conventional detection and grazing angle probe beam.

FIG. 3 is a schematic representation of a surface particle detector employing a virtual reference beam, conventional detection and a probe beam incident on the workpiece at a grazing angle.

A laser 10 transmits a beam of energy to beam splitter 12 where the beam is split into a probe beam 64 and a beam 66. The beam 66 reflects from reflector 18 to Bragg cell 30 where the reference beam 68 exits having a wavelength which has been changed from the wavelength of beam 66. The reference beam 68 travels to a partial reflector 70 from which the reference beam is reflected directly to detector 72, without being incident at the workpiece surface 24. Such a reference beam is referred to as a virtual reference beam.

The probe beam 64 travels through a lens 74 and is incident on surface 24 at a grazing angle in the location of particle 28. A scattered probe beam 76 is reflected from the particle 28 in a direction substantially normal to the surface 24. Beam 76 travels through lens 78, partial reflector 70 and is received at detector 72.

Since the wavelengths of the virtual reference beam 68 and the probe beam 76 from particle 28 are different, detector 72 will generate a beat frequency signal by means of a conventional heterodyne arrangement, indicative of the presence of particle 28 at the location where the probe beam 64 is incident at the surface 24.

In the absence of a particle or asperity 28, the probe beam 64 will reflect from surface 24 and continue to travel as beam 80 without being received by detector 72.

Figure 4:
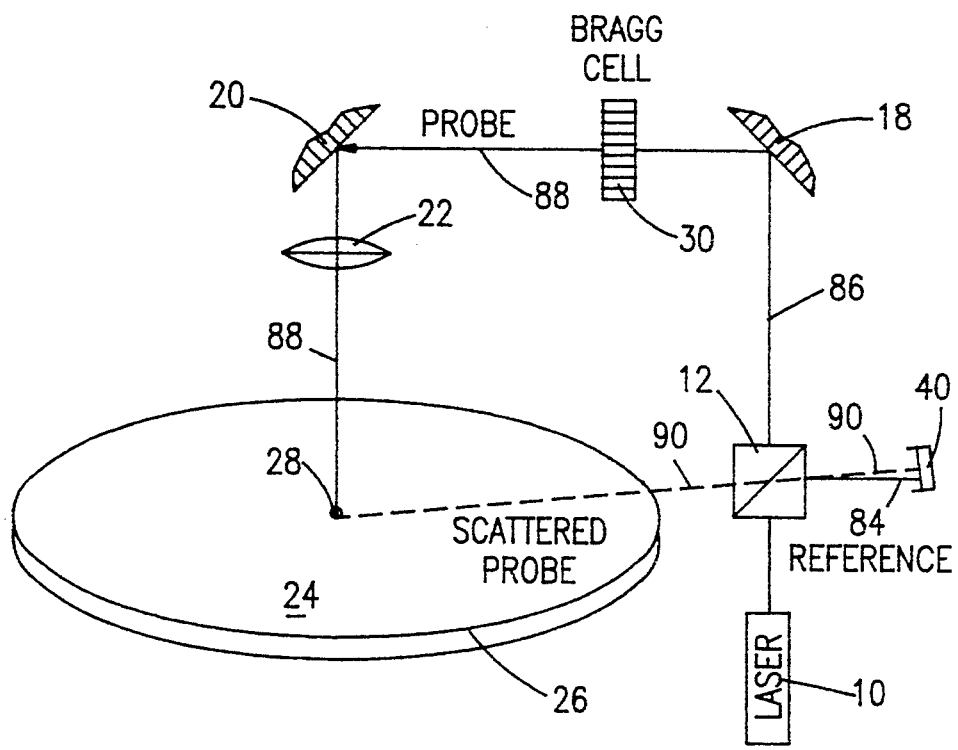
FIG. 4 is a schematic representation of another preferred embodiment of the invention including a virtual reference beam, Lloyd's mirror detection and a normal angle probe beam.

FIG. 4 schematically illustrates another alternative embodiment for practicing the invention employing a virtual reference beam, Lloyd's mirror detection and a probe beam incident on the workpiece at an angle substantially normal to the surface.

A laser 10 transmits a beam of energy to a beam splitter 12 from which a reference beam 84 and probe beam 86 exit. The reference beam 84 travels to detector 40.

The probe beam 86 is reflected by reflector 18 to a Bragg cell 30 where the wavelength of the beam is changed. The probe beam 88 exiting from the Bragg cell 30 is reflected by reflector 20 and travels through lens 22 to be incident at the workpiece surface 24 at the location of particle 28 at an angle substantially normal to the workpiece surface. Upon the probe beam 88 intercepting a particle or asperity 28, a scattered probe beam 90 is reflected which travels through beam splitter 12 to detector 40.

Since the wavelength of the scattered probe beam 90 and the wavelength of the virtual reference beam 84 are different, Lloyd's mirror detector 40 will generate a beat frequency signal indicative of the presence of particle 28 on the workpiece surface 24.

Figure 5:
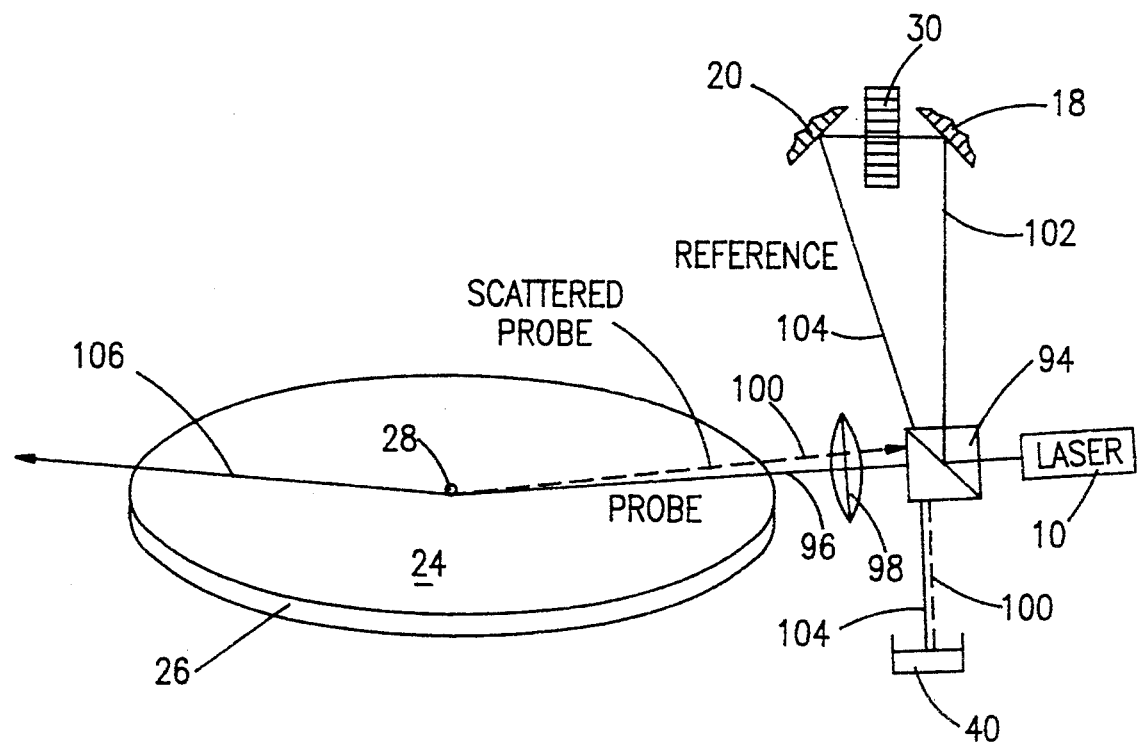
FIG. 5 is a schematic representation of another preferred embodiment of the invention including a virtual reference beam, Lloyd's mirror detection and a grazing angle probe beam.

FIG. 5 schematically illustrates a further embodiment of the invention employing a virtual reference beam, Lloyd's mirror detection and a probe beam incident on the workpiece at a grazing angle.

A laser 10 transmits a beam of energy into a beam splitter 94. A probe beam 96 exits the beam splitter and travels through a lens 98 and is incident on the workpiece surface 24 at a grazing angle in the location of a particle 28. Upon interception a particle, a scattered probe beam 100 is reflected back through lens 98 to beam splitter 94 from which the scattered probe beam is received at Lloyd's mirror detector 40.

Beam 102 exiting the beam splitter 94 is reflected by reflector 18 through a Bragg cell 30 when the wavelength of the beam 102 is changed. The reference beam 104 is reflected at a second reflector 20 from which the beam 104 travels through beam splitter 94 and is received at detector 40 as a virtual reference beam 104.

Since the wavelength of the virtual reference beam 104 and scattered probe beam 100 are different, Lloyd's mirror detector 40 will generate a beat frequency signal indicative of the presence of a particle 28 on the workpiece surface 24 at the location of the incident grazing angle probe beam 96.

In the absence of a particle or asperity 28, the incident grazing angle probe beam 96 will be reflected from the surface 24 as beam 106 and a scattered probe beam will not be detected at detector 40.

In a modification of the embodiment shown in FIG. 2, a HeNe laser beam travelled through a focussing lens into a Bragg cell. A polarizer and rotator was inserted into the path of the reference beam to minimize the effect of scattering in the Bragg cell. After reflection from either silicon or ceramic workpieces the reference beam travelled through a lens to a detector. In practice, the detector was able to generate 50 dB of signal range as the target was varied from bare silicon to a surface containing rough particles of approximately 10 micron diameter. Much of the background signal appeared to derive from scatter within the Bragg cell. The scatter derived within the Bragg cell can be eliminated in a number of ways. For example the background noise was substantially decreased for a shear wave Bragg cell by passing the two output beams from the Bragg cell through two orthogonally polarized filters.

Figure 6:
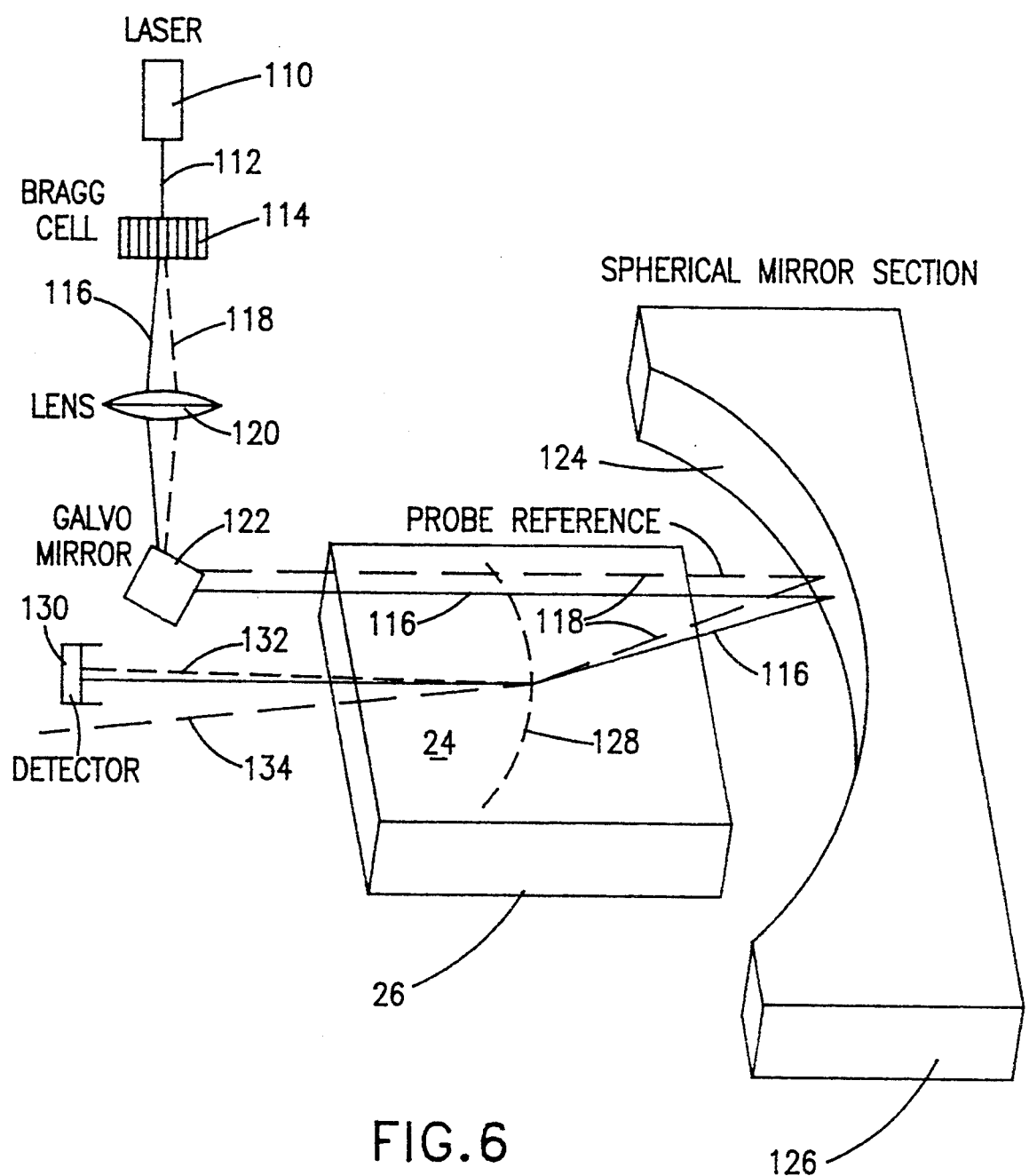
FIG. 6 is a schematic representation of a preferred embodiment of the invention incorporating a hyper telecentric scanner into the arrangement shown in FIG. 2.

FIG. 6 schematically illustrates a preferred embodiment of the invention incorporating a hyper-telecentric scanner into the arrangement shown in FIG. 2, which embodiment is particularly useful for in-situ contamination measurements. A laser 110 transmits a beam of energy 112 into a Bragg cell 114. Exiting the Bragg cell are a reference beam 116 and a probe beam 118 having different wavelengths. The beams 116, 118 are focussed by lens 120 onto an oscillating galvo-mirror 122. The reference beam 116 and probe beam 118 are reflected from galvo-mirror 122 to a reflecting surface 124 of spherical mirror section 126 from which the beams are reflected and are incident on the surface 24 of a workpiece 26 at a grazing angle to intersect along scan line 128.

The reference beam 116 is made to intercept the galvo-mirror 122 at the point axis of the galvo-mirror so that the reference beam is always received by detector 130 after reflecting from the surface 24 or from a particle on the surface.

The probe beam 118 intercepts the galvo-mirror 122 off-axis so that when the probe beam 118 reflected from mirror 126 intercepts a particle on the surface 24, a scattered probe beam 132 is received at detector 130. In the absence of a particle, the probe beam 118 is reflected from the surface 24 as beam 134 and is not received at the detector 130.

Preferably, the detector 130 is a Lloyd's mirror detector which will generate a beat frequency signal when a particle is intercepted by the scanning probe beam.

The advantages provided by the embodiment shown in FIG. 6 are the combination of a darkfield detection and Lloyd's mirror, the low vertical profile of the embodiment, the detection in the near forward scatter direction, the ability to quickly scan large workpiece surface areas and the insensitivity of the design to stray light.

It will be apparent to those skilled in the art that, if desired, the workpiece 26 may be mounted on an x-y table (not shown) for causing the workpiece to undergo two dimensional motion for scanning the entire surface 24 or a predetermined portion of the surface for particles.

Figure 7:
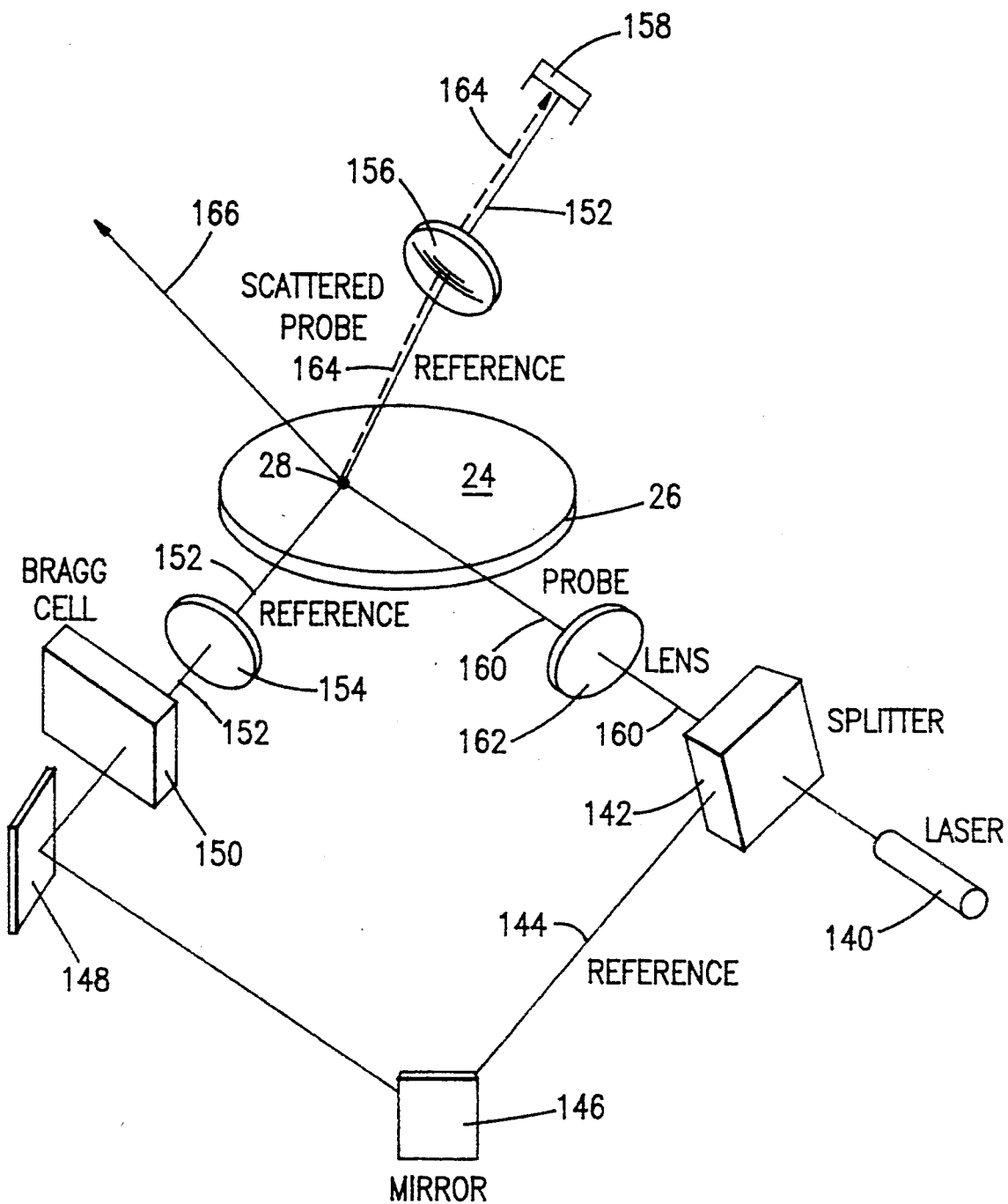
FIG. 7 is a schematic representation of a preferred embodiment incorporating a Bragg cell scanner in a perpendicular azimuthal direction in the arrangement shown in FIG. 2.

FIG. 7 schematically illustrates an embodiment of the invention incorporating a Bragg cell scanner in a perpendicular azimuthal direction in the arrangement shown in FIG. 2, which embodiment is more suited for high sensitivity scanning. As will be described below, the probe beam and reference beam are both incident on the surface 24 of the workpiece 26 at grazing angles, but the two beams have their respective azimuthal angles separated by approximately 90°. Since many workpieces contain patterns exhibiting rectangular geometries, which patterns scatter light predominantly along the rectangular axes, illumination and detection at ±45° to these axes will minimize the signal scattered from the pattern, thereby facilitating detection of particles in accordance with the teachings of the present invention. There is also coincidence detection where the particle must appear to protrude above the dominant mirror plane of the surface from two different points of view. The embodiment utilizes the ability of a Bragg cell to cause the laser to quickly scan the surface. The frequency at which the detector demodulates the signal must be synchronous with the Bragg frequency. Finally, there is compensation for the relatively large spot size that a grazing incidence laser beam generates by causing the region of detection sensitivity to be confined to the narrower dimension of each beam profile. For example, if each beam, the reference beam and the probe beam, illuminate a region of roughly 10 by 100 microns, the region over which the detector will be detecting particles is 10 by 10 microns. The result is a reduction of the affect of pattern and surface roughness on the measurements.

Referring to FIG. 7, a laser 140 transmits a beam of energy to a beam splitter 142. An exiting beam 144 is reflected at reflector 146 to a reflector 148 from which the beam enters a Bragg cell 150 where the beam wavelength is changed. The reference beam 152 from Bragg cell 150 is focussed by lens 154 to a location on the surface 24 of workpiece 26. The incidence angle of the reference beam 152 is adjusted at a grazing angle so that the reference beam is reflected from the surface 24 through lens 156 to detector 158 or is forward scattered from a particle 28 on surface 24 through lens 156 to detector 158.

The exiting probe beam 160 from beam splitter 142 passes through lens 162 and is focussed on the workpiece surface 24 at a grazing angle to intercept the reference beam 152 at a substantially orthogonal angle. The reflectors 146 and 148 are positioned to cause the reference beam 152 and the probe beam 160 to intercept at a substantially orthogonal angle.

Upon intercepting a particle or asperity 28 a scattered probe beam 164 is reflected from the particle through lens 156 to the detector 158.

Since the wavelengths of the reference beam 152 and probe beam 164 are different, the detector generates a beat frequency signal indicator of a particle in the spot where the two mentioned beams intersect.

If the probe beam 160 is not incident on a particle, the probe beam is reflected from surface 24 as beam 166 and is not detected at detector 158.

The advantages of the embodiment shown in FIG. 7 are the low profile of the arrangement, the ±45° coincidence with respect to the x-axis and y-axis coordinates of the workpiece pattern, small sensing area at the intersection of the reference beam and probe beam to reduce pattern and surface roughness effects, the combination of darkfield and Lloyd's mirror light discrimination and the fast Bragg cell spot scanning.

It will be apparent to those skilled in the art that there are alternative embodiments and methods for generating a probe beam and a reference beam having different wavelengths useful in practicing the present invention. For example, a Zeeman split laser produces two laser beams separated in frequencies and hence wavelengths. Alternatively, two separate lasers can be used to generate laser beams having different wavelengths.

Phase modulation methods exist for introducing periodic phase shifts in an optical beam. These methods include electrooptic phase retarders and rotating quarter- or multi-wave plates. Such methods can be considered as producing a beam having a wavelength different than the wavelength of the original beam, and as such could be used to create a heterodyne interferometer, provided the beams meet the following two conditions. First, the amount of phase shift must be more than ±90° (or else all possible phase combinations between the phase shifted and phase unshifted beams are not sampled). Second, the maximum difference in frequency between the shifted and unshifted beams should be greater than either the base band noise sources (typically about 10 kilohertz) or the modulation frequency induced by scanning either the probe beam or the reference beam across the workpiece (which can be as high as 50 megahertz). If both these conditions are met, beams are produced which are useful in practicing the present invention.

The above described invention has application for in-situ inspection inside manufacturing processing tools and for surface particle detection in general and for applications where stray light presents special problems in particular.

While there has been described and illustrated a preferred embodiment of the present invention and several modifications and variations thereof, it will be apparent to those skilled in the art that further modifications and variations are possible without deviating from the broad principle and spirit of the present invention which shall be limited solely by the scope of the claims appended hereto.

What is claimed is:

1. A surface particle detection apparatus comprising:
means for generating a probe beam and a reference beam at different wavelengths and for illuminating a surface with said probe beam; and
detector means for detecting a scattered probe beam arising from said probe beam intersecting a particle on the surface, and for simultaneously detecting a second beam spatially coherent with said scattered probe beam, said second beam comprising one of: (a) a real reference beam arising from said reference beam intercepting the surface at a grazing angle, and (b) a virtual reference beam arising from said reference beam bypassing the surface when at least one of said probe beam and scattered probe beam intercepts the surface at a grazing angle, said detector means generating a beat frequency signal resulting from interference of the detected beams at the detector means, said beat frequency signal being indicative of the presence of a particle on the surface.

2. A surface particle detection apparatus as set forth in claim 1 wherein said detector means comprises a Lloyd's mirror detector.

3. A surface particle detection apparatus as set forth in claim 2 wherein said means for generating causes said probe beam to be incident at the surface at an angle of incidence substantially normal to the surface and said reference beam to be incident at the surface at a grazing angle and said probe beam and said reference beam to intersect at substantially the same location at the surface.

4. A surface particle detection apparatus as set forth in claim 2 wherein said means for generating causes said probe beam and said reference beam to be incident at the surface at respective grazing angles and said probe beam and said reference beam to intersect at substantially the same location at the surface.

5. A surface particle detection apparatus as set forth in claim 4, wherein said means for generating further comprises hyper-telecentric scanning means.

6. A surface particle detection apparatus as set forth in claim 5, wherein is said hyper-telecentric scanning means comprises galvo-mirror means.

7. A surface particle detection apparatus as set forth in claim 6 wherein said hyper-telecentric scanning means further comprises spherical mirror means.

8. A surface particle detection apparatus as set forth in claim 4, wherein said means for generating further comprises means for causing said probe beam and said reference beam to intersect at a substantially orthogonal azimuthal angle.

9. A surface particle detection apparatus as set forth in claim 2 wherein said means for generating causes said probe beam to be incident at the surface at an angle substantially normal to the surface and said reference beam to be detected as a virtual reference beam.

10. A surface particle detection apparatus as set forth in claim 2 wherein said means for generating causes said probe beam to be incident at the surface at a grazing angle and said reference beam to be detected as a virtual reference beam.

11. A surface particle detection apparatus as set forth in claim 1 wherein said detector means is a heterodyne detector.

12. A surface particle detection apparatus as set forth in claim 11 wherein said means for generating causes said probe beam to be incident at the surface at a grazing angle and said reference beam to be detected as a virtual reference beam.

13. A surface particle detection apparatus as set forth in claim 1 wherein said means for generating is selected from the group consisting of a laser and Bragg cell, a Zeeman split laser and two lasers.

14. A method of surface particle detection comprising the steps of:
generating a probe beam and a reference beam at different wavelengths;
illuminating a surface with said probe beam; and
detecting a scattered probe beam arising from said probe beam intercepting a particle on the surface and detecting simultaneously a second beam spatially coherent with said scattered probe beam, said second beam comprising one of (a) a real reference beam arising from said reference beam intercepting the surface at a grazing angle, and (b) a virtual reference beam arising from said reference beam bypassing the surface when at least one of said probe beam and said scattered probe beam intercepts the surface at a grazing angle, and generating a beat frequency signal from interference of the detected beams, said beat frequency signal being indicative of the presence of a particle on the surface.

15. A method of surface particle detection as set forth in claim 14 wherein said detecting comprises the step of Lloyd's mirror detection.

16. A method of surface particle detection as set forth in claim 15 wherein said illuminating a surface comprises the step of illuminating the surface with said probe beam at an angle of incidence substantially normal to the surface and illuminating the surface with said reference beam at a grazing angle and said probe beam and said reference beam intersecting at substantially the same location at the surface.

17. A method of surface particle detection as set forth in claim 15, wherein said illuminating a surface comprises the steps of illuminating the surface with said probe beam and said reference beam at respective grazing angles and said probe beam and said reference beam intersecting at substantially the same location at the surface.

18. A method of surface particle detection as set forth in claim 17, wherein said illuminating a surface comprising reflecting said probe beam and said reference beam from a hyper-telecentric scanning means.

19. A method of surface particle detection as set forth in claim 18, wherein said illuminating a surface further comprises reflecting said probe beam and said reference beam from an oscillating galvo-mirror.

20. A method of surface particle detection as set forth in claim 19 wherein said illuminating a surface further comprises reflecting said probe beam and said reference beam from a spherical mirror surface.

21. A method of surface particle detection as set forth in claim 17, wherein said illuminating a surface further comprises said probe beam and said reference beam intersecting at a substantially orthogonal azimuthal angle.

22. A method of surface particle detection as set forth in claim 15 wherein said illuminating a surface comprises illuminating the surface with said probe beam at an angle substantially normal to the surface and wherein said detecting comprises detecting a virtual reference beam.

23. A method of surface particle detection as set forth in claim 15, wherein said illuminating a surface comprises illuminating the surface with said probe beam at a grazing angle and said detecting comprises detecting a virtual reference beam.

24. A method of surface particle detection as set forth in claim 14, wherein said detecting comprises the step of heterodyne detection.

25. A method of surface particle detection as set forth in claim 24 wherein said illuminating a surface comprises illuminating the surface with said probe beam at a grazing angle and said detecting comprises detecting a virtual reference beam.

26. A method of surface particle detection as set forth in claim 14 wherein said generating comprises generating said probe beam and said reference beam by means selected from the group consisting of a laser and Bragg cell, a Zeeman split laser and two lasers.

* * * * *